United States Patent
Rapoport

(10) Patent No.: US 10,101,422 B2
(45) Date of Patent: Oct. 16, 2018

(54) EXTENDABLE RADIOFREQUENCY SHIELD FOR MAGNETIC RESONANCE IMAGING DEVICE

(71) Applicant: Aspect Imaging Ltd., Shoham (IL)

(72) Inventor: Uri Rapoport, Moshav Ben Shemen (IL)

(73) Assignee: ASPECT IMAGING LTD., Shoham (IL)

( * ) Notice: Subject to any disclaimer, the term of this patent is extended or adjusted under 35 U.S.C. 154(b) by 0 days.

(21) Appl. No.: 15/886,110

(22) Filed: Feb. 1, 2018

(65) Prior Publication Data
US 2018/0164391 A1   Jun. 14, 2018

Related U.S. Application Data

(63) Continuation of application No. 15/459,723, filed on Mar. 15, 2017.
(Continued)

(51) Int. Cl.
*G01R 33/422* (2006.01)
*A61B 5/055* (2006.01)
*A61G 11/00* (2006.01)

(52) U.S. Cl.
CPC .......... *G01R 33/422* (2013.01); *A61B 5/0555* (2013.01); *A61G 11/00* (2013.01)

(58) Field of Classification Search
CPC ...... G01R 33/422; A61B 5/0555; A61G 11/00
See application file for complete search history.

(56) References Cited

U.S. PATENT DOCUMENTS

| 3,504,932 A | 4/1970 | Kozowyk et al. |
| 3,534,251 A | 10/1970 | Richards |

(Continued)

FOREIGN PATENT DOCUMENTS

| DE | 202013105276 | 2/2014 |
| EP | 0825450 | 8/1997 |

(Continued)

OTHER PUBLICATIONS

Maramraju, Sri Harsha, et al. Electromagnetic interactions in a shielded PET/MRI system for simultaneous PET/MRI imaging in 9.4 T: evaluation and results, IEEE Transactions on Nuclear Science 59, 5 (2012): pp. 1892-1896.

*Primary Examiner* — Dixomara Vargas
(74) *Attorney, Agent, or Firm* — Pearl Cohen Zedek Latzer Baratz LLP

(57) ABSTRACT

A radiofrequency (RF) shielding channel for a magnetic resonance imaging (MRI) device is provided. The RF shielding channel can include at least one conductive layer having a proximal end and a distal end. The RF shielding channel can include a connector to removably attach the proximal end of the at least one conductive layer to a bore of the MRI device. The at least one conductive layer can be extended in a longitudinal direction with respect to the bore of the MRI device between a first predetermined longitudinal dimension and a second predetermined longitudinal dimension, such that a RF shield is formed from the bore of the MRI device to the distal end of the at least one conductive layer. The RF shield can prevent an external RF radiation from entering the bore of the MRI device and/or an RF radiation emitted by the MRI device from exiting the bore.

12 Claims, 14 Drawing Sheets

Related U.S. Application Data

(60) Provisional application No. 62/434,260, filed on Dec. 14, 2016.

(56) References Cited

U.S. PATENT DOCUMENTS

| | | | |
|---|---|---|---|
| 4,910,461 A * | 3/1990 | Van Vaals | G01R 33/34046 324/318 |
| 4,977,585 A | 12/1990 | Boyd | |
| 5,028,872 A * | 7/1991 | Nakabayashi | A61B 5/0555 324/318 |
| 5,039,826 A | 8/1991 | Newland | |
| 5,065,760 A | 11/1991 | Krause et al. | |
| 5,159,929 A | 11/1992 | Morris et al. | |
| 5,243,286 A | 9/1993 | Rzedzian et al. | |
| 5,305,749 A | 4/1994 | Li et al. | |
| 5,572,131 A | 11/1996 | Rzedzian | |
| 5,594,200 A | 1/1997 | Ramsey | |
| 5,635,889 A | 6/1997 | Stelter | |
| 5,986,531 A * | 11/1999 | Carrozzi | G01R 33/422 324/318 |
| RE36,679 E | 5/2000 | Zakhor et al. | |
| 6,215,309 B1 | 4/2001 | Rzedzian et al. | |
| 6,346,814 B1 * | 2/2002 | Carrozzi | A61B 5/0555 324/318 |
| 6,711,430 B1 * | 3/2004 | Ferris | A61B 5/0555 324/318 |
| 6,801,038 B2 * | 10/2004 | Carrozzi | A61B 5/0555 324/309 |
| 6,873,156 B2 * | 3/2005 | Ferris | A61B 5/0555 324/309 |
| 6,995,562 B2 | 2/2006 | Laskaris et al. | |
| 7,141,974 B2 * | 11/2006 | Edelstein | G01R 33/3854 324/318 |
| 7,157,911 B2 | 1/2007 | Suzuki et al. | |
| 7,171,256 B1 | 1/2007 | Graessle et al. | |
| 7,375,526 B2 * | 5/2008 | Edelstein | G01R 33/3854 324/307 |
| 7,529,575 B2 * | 5/2009 | Rezzonico | A61B 5/0555 324/318 |
| 7,633,294 B2 * | 12/2009 | Leussler | G01R 33/422 324/318 |
| 7,715,895 B1 | 5/2010 | Graessle et al. | |
| 7,772,503 B2 * | 8/2010 | Ginanneschi | G01R 33/422 174/378 |
| 7,801,613 B2 | 9/2010 | Li et al. | |
| 8,807,084 B2 | 8/2014 | Rapoport et al. | |
| 8,851,018 B2 | 10/2014 | Rapoport et al. | |
| 8,896,310 B2 | 11/2014 | Rapoport | |
| 9,301,724 B2 * | 4/2016 | McKnight | A61B 5/702 |
| 9,498,167 B2 * | 11/2016 | Mostafavi | A61B 5/064 |
| 9,562,956 B2 * | 2/2017 | Rapoport | G01R 33/288 |
| 2002/0057088 A1 * | 5/2002 | Carrozzi | A61B 5/0555 324/318 |
| 2003/0016518 A1 | 1/2003 | Arz | |
| 2003/0058502 A1 | 3/2003 | Griffiths et al. | |
| 2003/0088175 A1 | 5/2003 | Branch et al. | |
| 2005/0046422 A1 * | 3/2005 | Edelstein | G01R 33/3854 324/307 |
| 2005/0049491 A1 * | 3/2005 | Rezzonico | A61B 5/0555 600/436 |
| 2007/0026733 A1 | 2/2007 | Greim et al. | |
| 2007/0135704 A1 | 6/2007 | Branch et al. | |
| 2007/0232894 A1 | 10/2007 | Feenan | |
| 2008/0060843 A1 * | 3/2008 | Ginanneschi | G01R 33/422 174/378 |
| 2008/0094062 A1 * | 4/2008 | Edelstein | G01R 33/3854 324/318 |
| 2008/0186026 A1 * | 8/2008 | Leussler | G01R 33/422 324/318 |
| 2010/0000780 A1 | 1/2010 | Zhu et al. | |
| 2011/0162652 A1 | 7/2011 | Rapoport | |
| 2012/0046722 A1 | 2/2012 | Olsen et al. | |
| 2012/0071745 A1 | 3/2012 | Rapoport | |
| 2012/0118630 A1 | 5/2012 | Jiang et al. | |
| 2012/0119742 A1 | 5/2012 | Rapoport | |
| 2013/0229181 A1 * | 9/2013 | Biber | G01R 33/422 324/318 |
| 2013/0328560 A1 | 12/2013 | Rapoport | |
| 2014/0051976 A1 | 2/2014 | Rapoport et al. | |
| 2014/0117989 A1 * | 5/2014 | Rapoport | G01R 33/288 324/322 |
| 2014/0139216 A1 | 5/2014 | Rapoport | |
| 2014/0354279 A1 | 12/2014 | Dumoulin et al. | |
| 2014/0364722 A1 | 12/2014 | Dumoulin | |
| 2014/0378821 A1 | 12/2014 | Rapoport et al. | |
| 2015/0059655 A1 | 3/2015 | Rapoport | |
| 2015/0112186 A1 | 4/2015 | Rapoport et al. | |
| 2015/0137812 A1 | 5/2015 | Rapoport | |
| 2015/0141799 A1 | 5/2015 | Rapoport et al. | |
| 2015/0168519 A1 | 6/2015 | Rapoport | |
| 2015/0208994 A1 | 7/2015 | Rapoport | |
| 2015/0212172 A1 | 7/2015 | Rapoport | |
| 2015/0212173 A1 | 7/2015 | Rapoport | |
| 2015/0253400 A1 | 9/2015 | Rapoport | |
| 2015/0253401 A1 | 9/2015 | Rapoport | |
| 2017/0146619 A1 * | 5/2017 | Strauss | G01R 33/283 |
| 2017/0256853 A1 | 9/2017 | Anderson et al. | |

FOREIGN PATENT DOCUMENTS

| | | |
|---|---|---|
| JP | 62207448 | 9/1987 |
| JP | 2005270422 | 10/2005 |
| WO | WO2000001611 | 3/2000 |
| WO | WO2015071906 | 5/2015 |

* cited by examiner

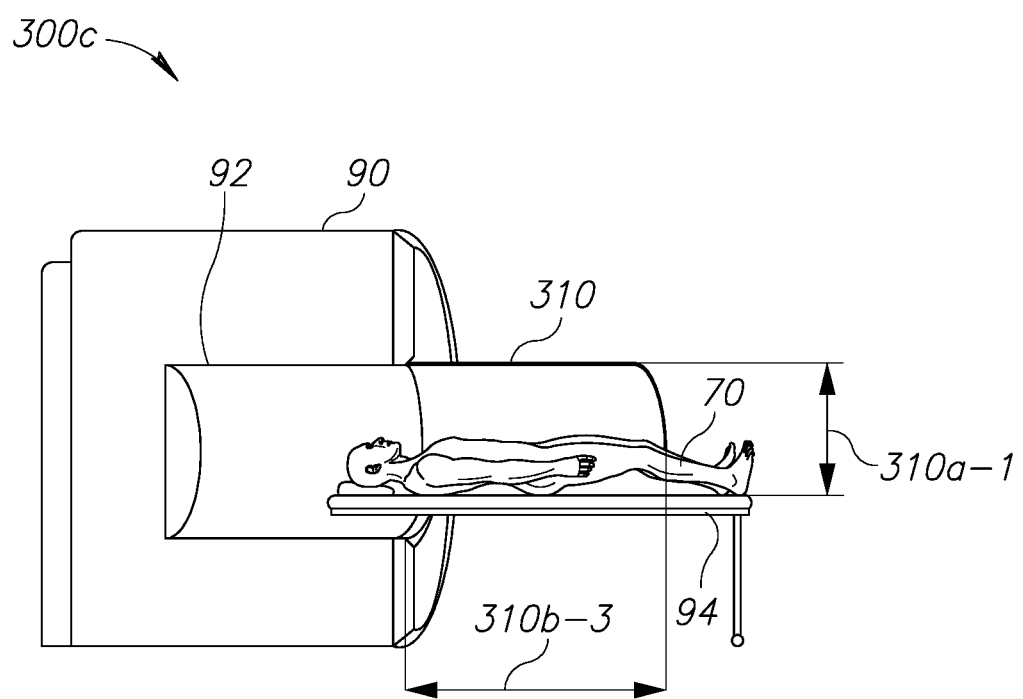
Figure 2B (cont. 1)

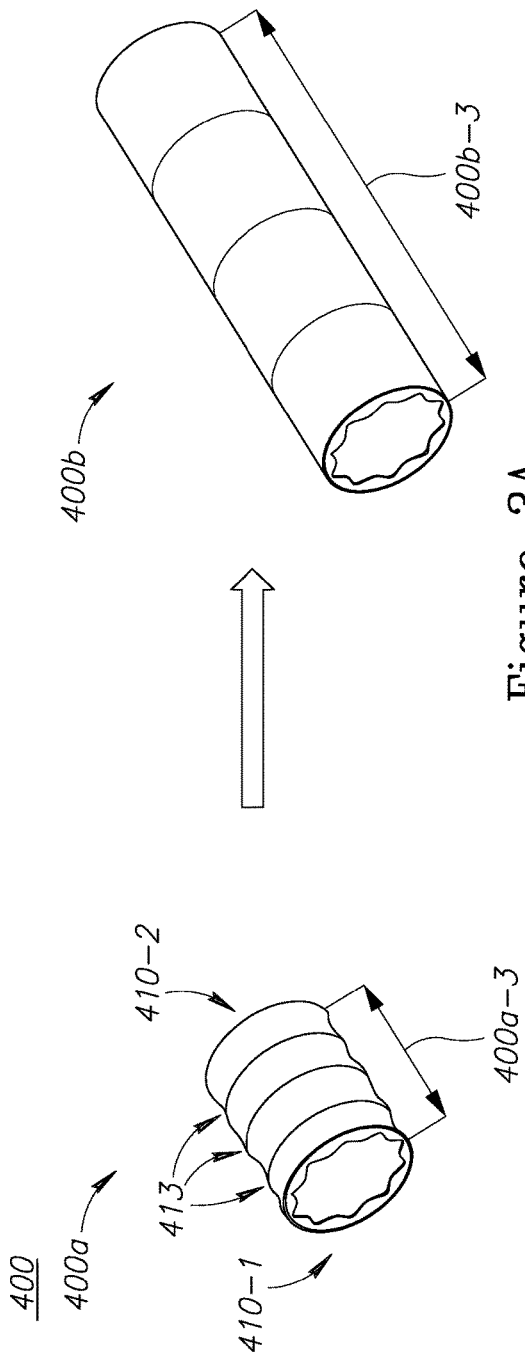
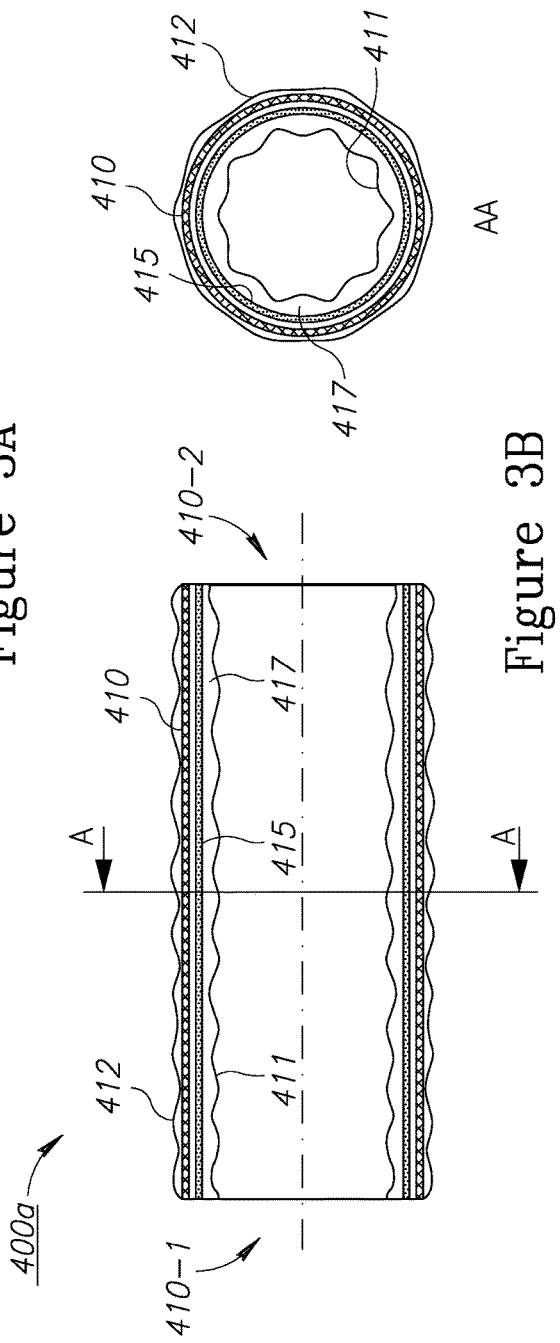
Figure 3A
Figure 3B

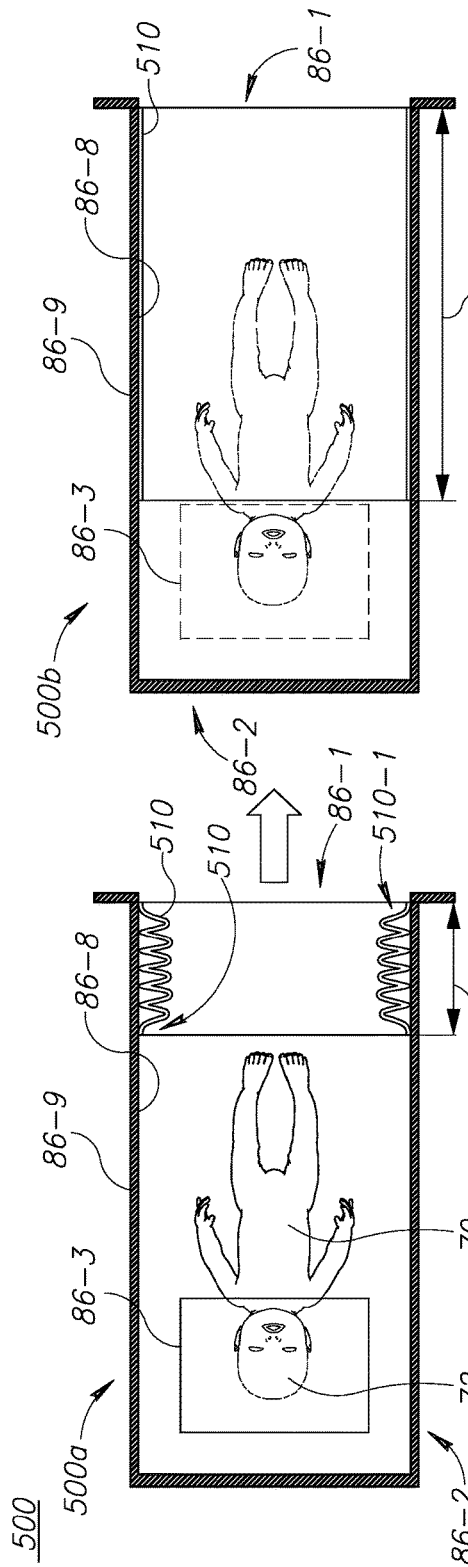
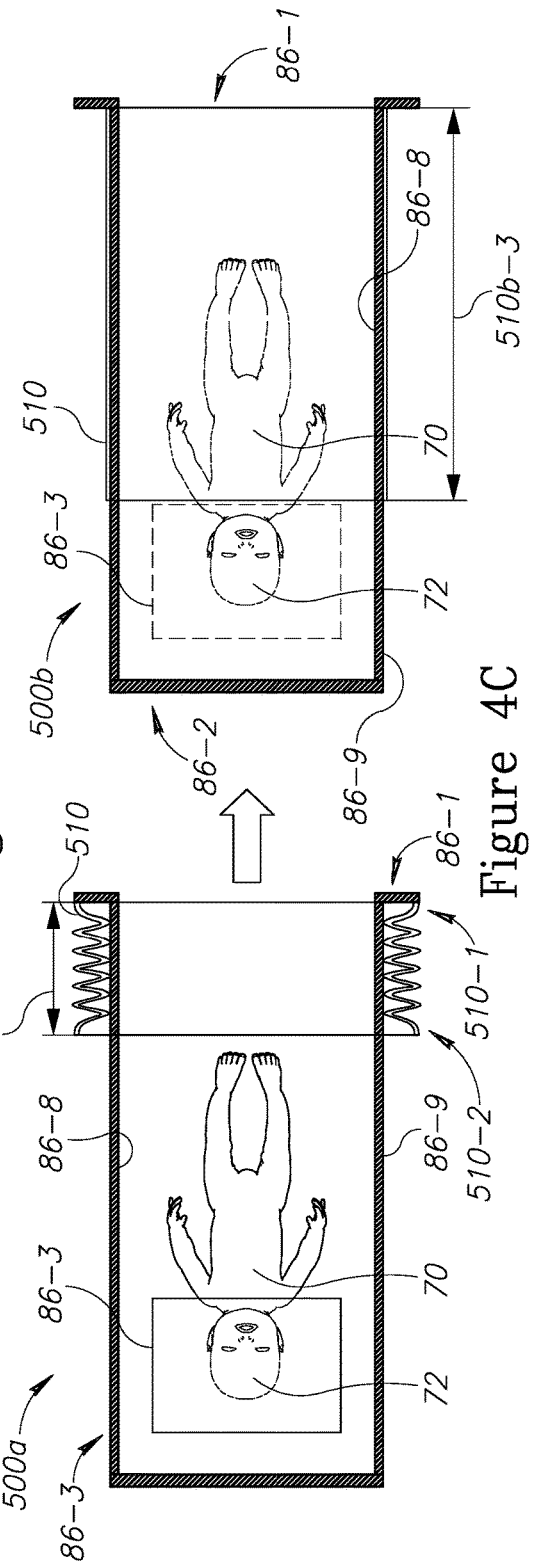
Figure 4B
Figure 4C

EXTENDABLE RADIOFREQUENCY SHIELD FOR MAGNETIC RESONANCE IMAGING DEVICE

CROSS REFERENCE TO RELATED APPLICATIONS

This application claims priority to U.S. application Ser. No. 15/459,723 filed on Mar. 15, 2017, which claims the benefit of and priority to U.S. Provisional Application No. 62/434,260 filed on Dec. 14, 2016, the entire contents of which are all incorporated herein by reference in their entireties.

FIELD OF THE INVENTION

The present invention relates to the field of magnetic resonance imaging systems, and more particularly, to radiofrequency radiation shielding.

BACKGROUND OF THE INVENTION

Magnetic resonance imaging (MRI) devices can emit radio waves at a radiofrequency (RF) that can cause disturbance and/or damage to surrounding electronic equipment (e.g., medical equipment, life support equipment). In some instances, it may be necessary to image a patient that is connected to life support (e.g., mechanical ventilation, oxygen, intravenous medications/hydration, etc.). The life support equipment can experience substantial interference from the RF.

External RF radiation (e.g., emitted by electric lines, radio signals, medical equipment, etc.) can interfere with MRI devices and/or can affect an operation of the MRI device. Accordingly, MRI devices are typically deployed in a dedicated MRI room to prevent from RF radiation emitted by MRI devices from exiting the MRI room and/or to prevent an external RF radiation from entering the MRI room.

Deployment of MRI devices in RF shielded room can be expensive and can require dedicated space within a hospital, doctor's office and/or other institution using MRI devices. Therefore, it can be desirable to deploy MRI devices without requiring a RF shielded room.

SUMMARY OF THE INVENTION

One aspect of the present invention provides a radiofrequency (RF) shielding channel for a magnetic resonance imaging (MRI) device, the RF shielding channel includes: at least one conductive layer having a proximal end and a distal end, the at least one conductive layer extendable in a longitudinal direction with respect to a bore of the MRI device between a first predetermined longitudinal dimension and a second predetermined longitudinal dimension; and a connector to connect the proximal end of the at least one conductive layer to the bore of the MRI device, such that a RF shield is formed from the bore of the MRI device to the distal end of the at least one conductive layer upon extension of the at least one conductive layer to the second predetermined longitudinal dimension.

In some embodiments, the RF shielding channel further includes: an inner layer and an outer layer surrounding the at least one conductive layer and connected to the distal end of the at least one conductive layer, the inner layer and the outer layer are made of foldable material and comprising a plurality of folds, wherein the inner layer and the outer layer unfold, upon extension of the at least one conductive layer to the second predetermined longitudinal dimension, and fold, upon contraction of the at least one conductive layer to the first predetermined longitudinal dimension.

In some embodiments, the RF shielding channel further includes: an extendable layer positioned between the inner layer and the outer layer and connected to the distal end of the at least one conductive layer, wherein the extendable layer to extend the at least one conductive layer to the second predetermined longitudinal dimension and to unfold the inner layer and the outer layer, and wherein the extendable layer to contract the at least one conductive layer to the first predetermined longitudinal dimension and to fold the inner layer and the outer layer.

In some embodiments, the RF shielding channel further includes a gap between the inner layer and the extendable layer, wherein the gap comprises a fluid.

In some embodiments, the extendable layer extends upon an increase of a fluid pressure within the gap and wherein the extendable layer contracts upon decrease of the fluid pressure within the gap.

In some embodiments, the at least one conductive layer having a transverse dimension and wherein a ratio of the second predetermined longitudinal dimension to the transverse dimension is at least 5:1.

In some embodiments, the at least one conductive layer having a tapered shape in the longitudinal direction with respect to the bore of the MRI device.

In some embodiments, the at least one conductive layer having a substantially U-shape transversal cross-section and wherein the at least one conductive layer is connected to a bed of the MRI device such that the bed being a part of the RF shielding channel.

In some embodiments, the proximal end of the at least one conductive layer is connected to an aperture of the bore of the MRI device.

In some embodiments, the at least conductive layer at least partly envelops at least a portion of a patient that is not being imaged by the MRI device.

In some embodiments, an electrical path is established between the at least one conductive layer and the bore of the MRI device.

In some embodiments, the MRI device utilizes at least one of: permanent magnets, superconductive magnets or any combination thereof to generate a magnetic field.

Another aspect of the present invention provides a radiofrequency (RF) shielding channel for an incubator for positioning a neonate within a magnetic resonance imaging (MRI) device, the RF shielding channel includes: at least one conductive layer having a proximal end and a distal end, the at least one conductive layer extendable in a longitudinal direction with respect to a longitudinal axis of the incubator between a first predetermined longitudinal dimension and a second predetermined longitudinal dimension; and a connector to connect the proximal end of the at least one conductive layer to a proximal end of the incubator, such that a RF shield is formed from the proximal end of the incubator to the distal end of the at least one conductive layer, upon extension of the at least one conductive layer to the second predetermined longitudinal dimension, wherein the incubator is inserted into the bore of the MRI device via a distal end of the incubator such that the proximal end of the incubator mates with an aperture of the bore In some embodiments, the RF shielding channel further includes: an inner layer and an outer layer surrounding the at least one conductive layer and connected to the distal end of the at least one conductive layer, the inner layer and the outer layer are made of foldable material and comprising a plurality of folds, wherein the inner layer and the outer layer unfold, upon extension of the at least one conductive layer to the second predetermined longitudinal dimension, and fold, upon contraction of the at least one conductive layer to the first predetermined longitudinal dimension.

In some embodiments, the RF shielding channel further includes an extendable layer positioned between the inner layer and the outer layer and connected to the distal end of the at least one conductive layer, wherein the extendable layer to extend the at least one conductive layer to the second predetermined longitudinal dimension and to unfold the inner layer and the outer layer, and wherein the extendable layer to contract the at least one conductive layer to the first predetermined longitudinal dimension and to fold the inner layer and the outer layer.

In some embodiments, the RF shielding channel further includes a gap between the inner layer and the extendable layer, wherein the gap comprises a fluid.

In some embodiments, the extendable layer extends upon an increase of a fluid pressure within the gap and wherein the extendable layer contracts upon decrease of the fluid pressure within the gap.

In some embodiments, the proximal end of the at least one conductive layer is connected to at least one internal surface of the incubator.

In some embodiments, the proximal end of the at least one conductive layer is connected to at least one external surface of the incubator.

In some embodiments, the at least one conductive layer having a transversal dimension and wherein a ratio of the second predetermined longitudinal dimension to the transverse dimension is at least 5:1.

These, additional, and/or other aspects and/or advantages of the present invention are set forth in the detailed description which follows; possibly inferable from the detailed description; and/or learnable by practice of the present invention.

BRIEF DESCRIPTION OF THE DRAWINGS

For a better understanding of embodiments of the invention and to show how the same may be carried into effect, reference will now be made, purely by way of example, to the accompanying drawings in which like numerals designate corresponding elements or sections throughout.

In the accompanying drawings:

FIGS. 3A-3B are illustrations of a radiofrequency (RF) shielding channel for a magnetic resonance imaging (MRI) device, including multiple layers, according to some embodiments of the invention;

FIGS. 4A-4C are illustrations of a radiofrequency (RF) shielding channel for an incubator for positioning a neonate in a magnetic resonance imaging (MRI) device, according to some embodiments of the invention;

DETAILED DESCRIPTION OF THE INVENTION

Figure 1A:
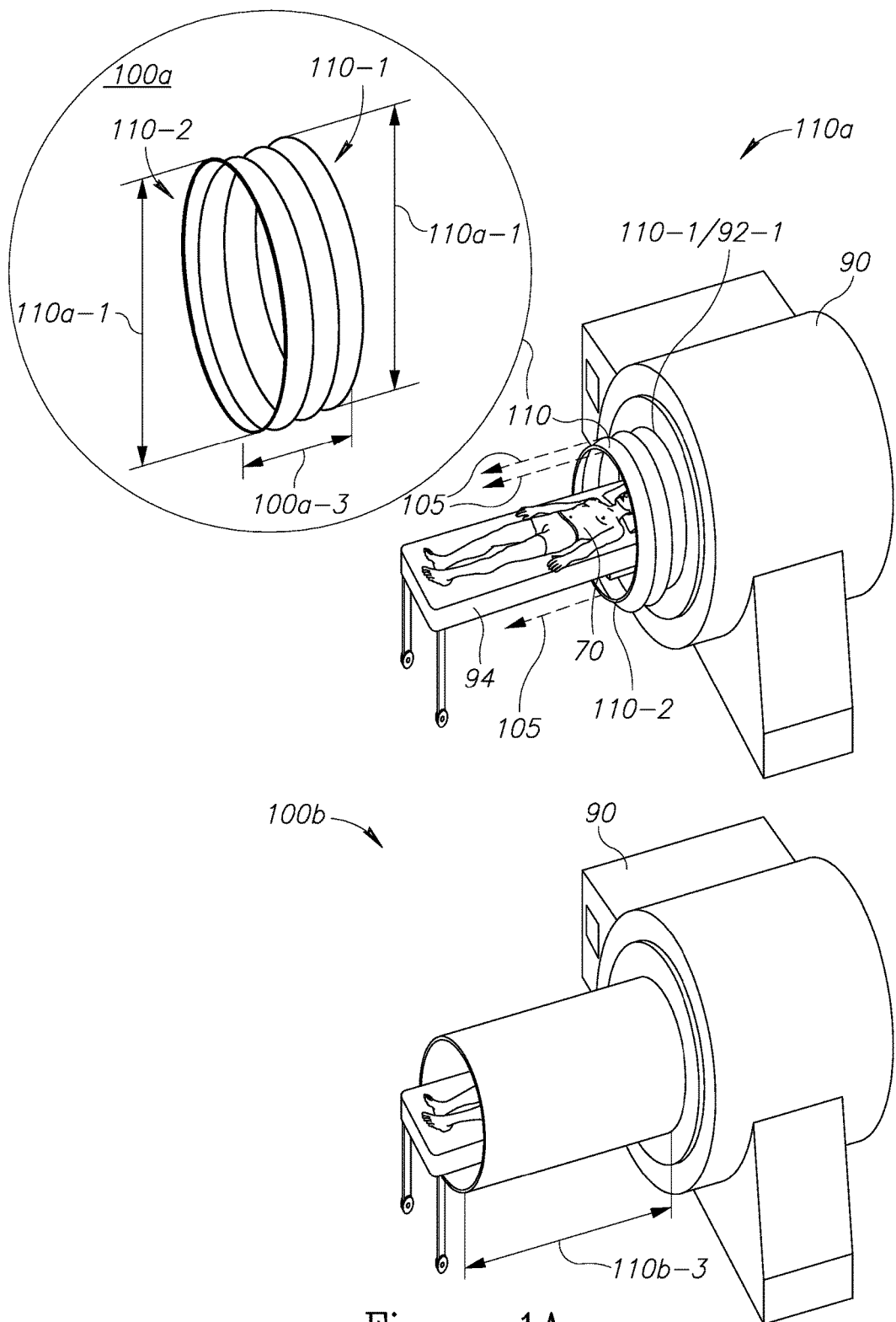
FIGS. 1A-1C are illustrations a radiofrequency (RF) shielding channel for a magnetic resonance imaging (MRI) device, including at least one conductive layer, according to some embodiments of the invention.

In the following description, various aspects of the present invention are described. For purposes of explanation, specific configurations and details are set forth in order to provide a thorough understanding of the present invention. However, it will also be apparent to one skilled in the art that the present invention may be practiced without the specific details presented herein. Furthermore, well known features may have been omitted or simplified in order not to obscure the present invention. With specific reference to the drawings, it is stressed that the particulars shown are by way of example and for purposes of illustrative discussion of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

Before at least one embodiment of the invention is explained in detail, it is to be understood that the invention is not limited in its application to the details of construction and the arrangement of the components set forth in the following description or illustrated in the drawings. The invention is applicable to other embodiments that may be practiced or carried out in various ways as well as to combinations of the disclosed embodiments. Also, it is to be understood that the phraseology and terminology employed herein is for the purpose of description and should not be regarded as limiting.

Generally, a radiofrequency (RF) shielding channel for a magnetic resonance imaging (MRI) device is provided. The RF shielding channel can include at least one conductive layer having a proximal end and a distal end. The RF shielding channel can include a connector to removably attach the proximal end of the at least one conductive layer to a bore of the MRI device. The at least one conductive layer can be extended in a longitudinal direction with respect to the bore of the MRI device between a first predetermined longitudinal dimension and a second predetermined longitudinal dimension, such that a RF shield is formed from the bore of the MRI device to the distal end of the at least one conductive layer. The RF shield can prevent an external RF radiation from entering the bore of the MRI device and/or an RF radiation emitted by the MRI device from exiting the bore.

Figure 1B:
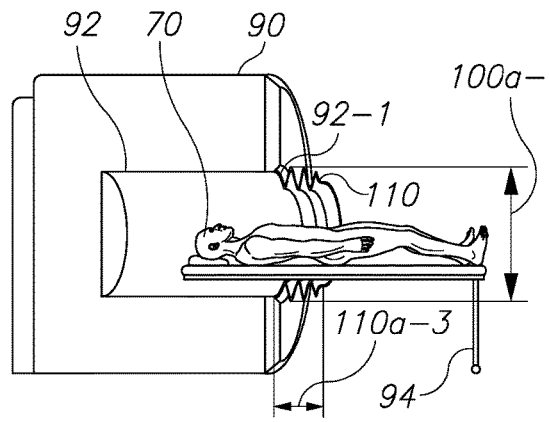
Figure 1B:
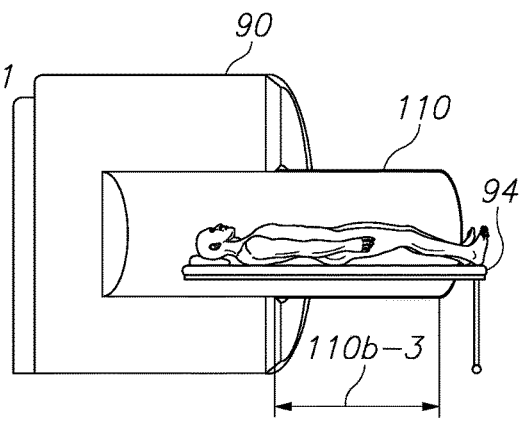
Figure 1C:
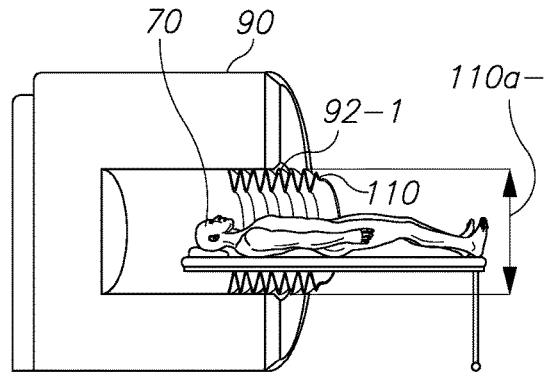
Figure 1C:
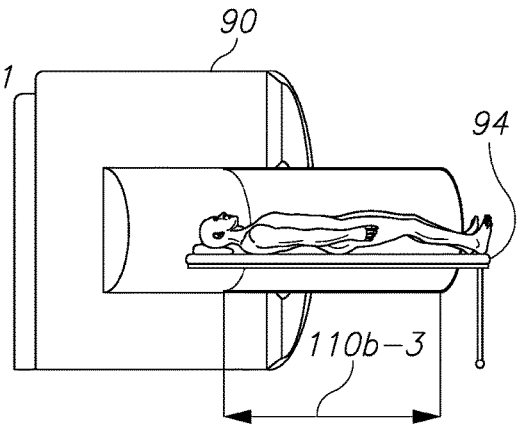

FIGS. 1A-1C are illustrations a radiofrequency (RF) shielding channel 100 for a magnetic resonance imaging (MRI) device 90, including at least one conductive layer 110, according to some embodiments of the invention. Illustration 100a and illustration 100b in FIGS. 1A-1C show an initial state and extended state of the RF shielding channel 100, respectively.

The radiofrequency (RF) shielding channel 100 can include at least one conductive layer 110. The at least one conductive layer 110 can be a net made of an electrically conductive and/or nonmagnetic metal (e.g., copper, aluminum, and/or other suitable material as is known in the art). The at least one conductive layer 110 can include a proximal end 110-1 and a distal end 110-2. In some embodiments, the at least one conductive layer 110 has a substantially annular cross-section. The proximal end 110-1 and the distal end 110-2 of the at least one conductive layer 110 can have a first transverse dimension (e.g., a first diameter) 110a-1.

The RF shielding channel 100 can include a connector (not shown) to removably attach the proximal end 110-1 of the at least one conductive layer 110 to a bore 92 of the MRI device 90, such that an electrical path can be established between the at least one conductive layer 110 and the bore 92. In some embodiments, the MRI device 90 utilizes at least one permanent magnet to generate a magnetic field.

The at least one conductive layer 110 can be extended in a longitudinal direction 105 with respect to the bore 92 of the MRI device (e.g., indicated by dashed arrows in FIG. 1A) from a first predetermined longitudinal dimension 110a-3 to a second predetermined longitudinal dimension 110b-3 (e.g., from the initial state 100a to the extended state 100b, as shown in FIG. 1A). The at least one conductive layer 110 in the extended state 100b can, for example, envelop at least a portion of a patient 70 that is not being imaged. A ratio of the second predetermined longitudinal dimension 110b-3 to the first transversal dimension (e.g., the first diameter) 110a-1 of the proximal end 110-1 can be at least one 5:1, such that a RF shield is formed (e.g., by the at least one conductive layer 110 in the extended state 100b) from the bore 92 of the MRI device 90 to the distal end 110-2 of the at least one conductive layer 110. The RF shield can provide a RF shielding of the MRI device 90. The RF shielding of the MRI device 90 can include preventing an external RF radiation from entering the bore 92 of the MRI device 90 and/or an RF radiation emitted by the MRI device 90 from exiting the bore 92.

The at least one conducive layer 110 can be contracted from the second predetermined longitudinal dimension 110b-3 to the first predetermined longitudinal dimension 110a-3. In various embodiments, the at least one conductive layer 110 is extended and/or contracted manually and/or using a dedicated mechanism (not shown).

The proximal end 110-1 of the at least one conductive layer 110 can be removably attached to an aperture of the bore 92 (e.g., as shown in FIGS. 1A-1B). In some embodiments, the proximal end 110-1 of the at least one conductive layer 110 is removably attached to an interior portion of the bore 92 (e.g., as shown in FIG. 1C).

Figure 1D:
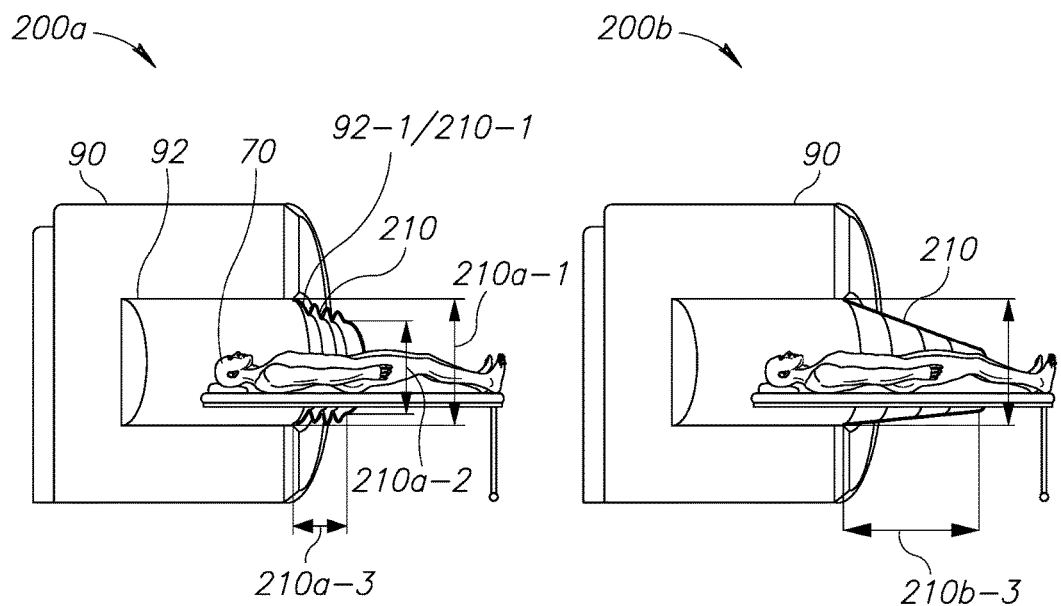
FIG. 1D is an illustration of a radiofrequency (RF) shielding channel for a magnetic resonance imaging (MRI) device, including at least one conductive layer having a tapered shape in a longitudinal direction along the conductive layer, according to some embodiments of the invention.

FIG. 1D is an illustration of a radiofrequency (RF) shielding channel 200 for a magnetic resonance imaging (MRI) device 90, including at least one conductive layer 210 having a tapered shape in a longitudinal direction along the conductive layer, according to some embodiments of the invention. Illustration 200a and illustration 200b in FIG. 1D show an initial state and an extended state of the RF shielding channel 200, respectively.

The RF shielding channel 200 can include at least one conductive layer 210 (e.g., a copper net) having a tapered shape in a longitudinal direction along the conductive layer. The at least one conductive layer 210 can have a proximal end 210-1 and a distal end 210-2. The proximal end 210-1 can have a first transverse dimension (e.g., a first diameter) 210a-1 (e.g., that can be identical to the first transverse dimension 110a-1 as shown in FIGS. 1A-1C) and/or the distal end 210-2 can have a second transverse dimension (e.g., a second diameter) 210a-2. The second transverse dimension 210a-2 can be smaller than the first transverse dimension 210a-1 (e.g., as shown in FIG. 1D).

The RF shielding channel 200 can include a connector (not shown) to removably attach the proximal end 210-1 of the at least one conductive layer 210 to the bore 92 of the MRI device 90, such that an electrical path can be established between the at least one conductive layer 210 and the bore 92.

The at least one conductive layer 210 can be extended in a longitudinal direction along the conductive layer between a first predetermined longitudinal dimension 210a-3 (e.g., that can be identical to the first predetermined dimension 110a-3 as shown in FIGS. 1A-1C) and a second predetermined longitudinal dimension 210b-3. The at least one conductive layer 210 in the extended state 200b can, for example, envelop at least a portion of a patient 70 that is not being imaged. A ratio of the second predetermined longitudinal dimension 210b-3 to the first transverse dimension 210a-1 of the proximal end 210-1 can be at least 5:1 to provide the RF shielding of the MRI device 90 (e.g., by the at least one conductive layer 210 in the extended state 200b), as described above with respect to FIGS. 1A-1C.

The second predetermined longitudinal dimension 210b-3 of the at least one conductive layer 210 having tapered shape in the longitudinal direction along the conductive layer (e.g., as shown in FIG. 1D) can be smaller compared to the second longitudinal dimension 110b-3 of the at least one conductive layer 110 having uniform cross-section along the conductive layer (e.g., as shown in FIGS. 1A-1C). Accordingly, distal end 210-2 of the at least one conductive layer 210 (e.g., as shown in FIG. 1D) can protrude from the bore 92 to a smaller distance compared to the distal end 110-2 of the at least one conductive layer 110 (e.g., as shown in FIG. 1A) in the extended states 200b, 100b, respectively.

Figure 2A:
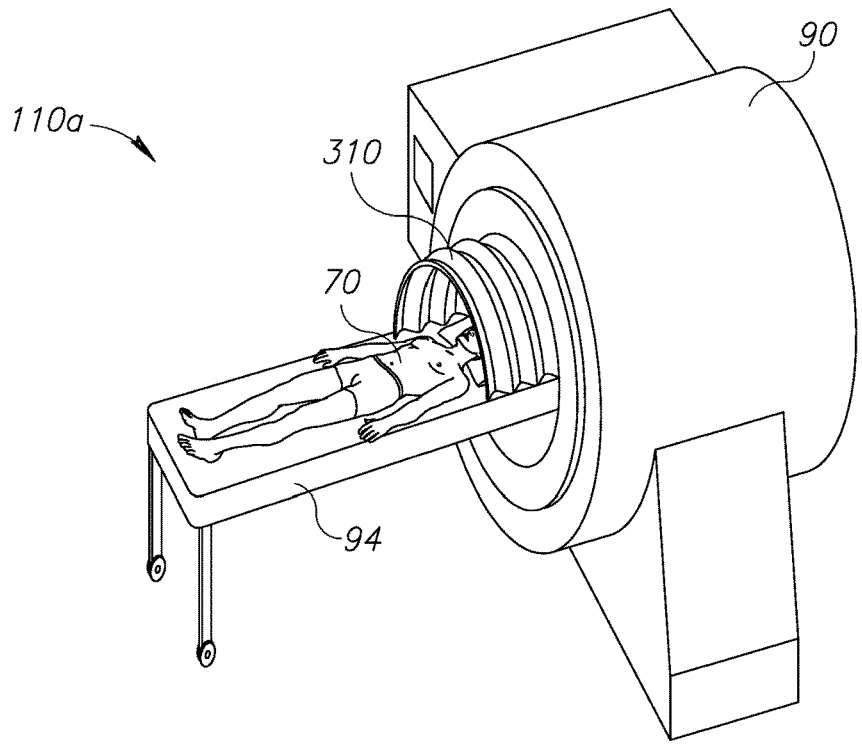
FIGS. 2A-2B are illustration of a RF shielding channel for a magnetic resonance imaging (MRI) device, including at least one conductive layer having a U-shape transverse cross-section, according to some embodiments of the invention.
Figure 2A:
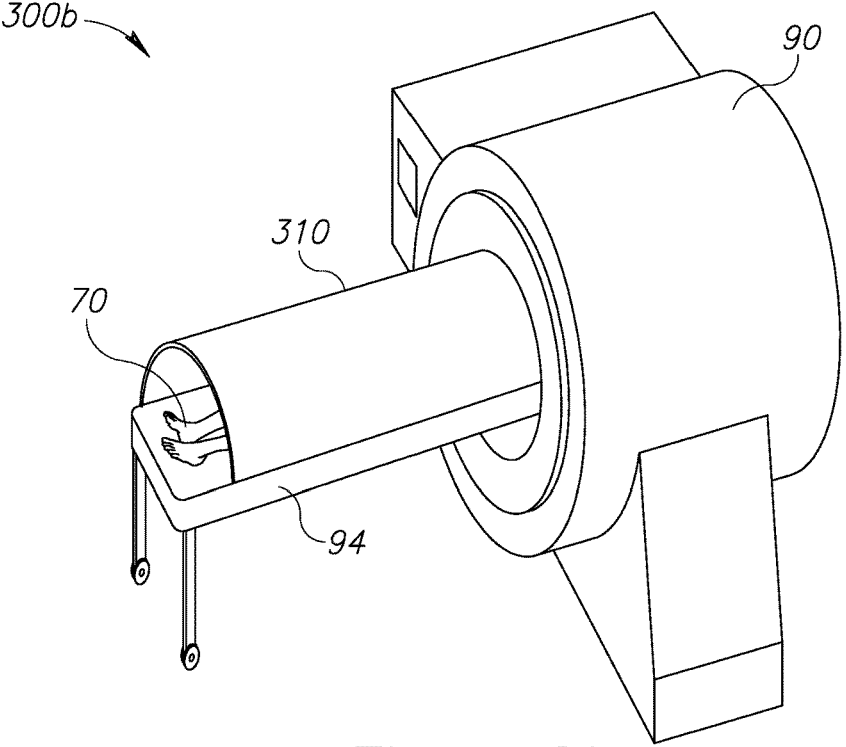
Figure 2B:
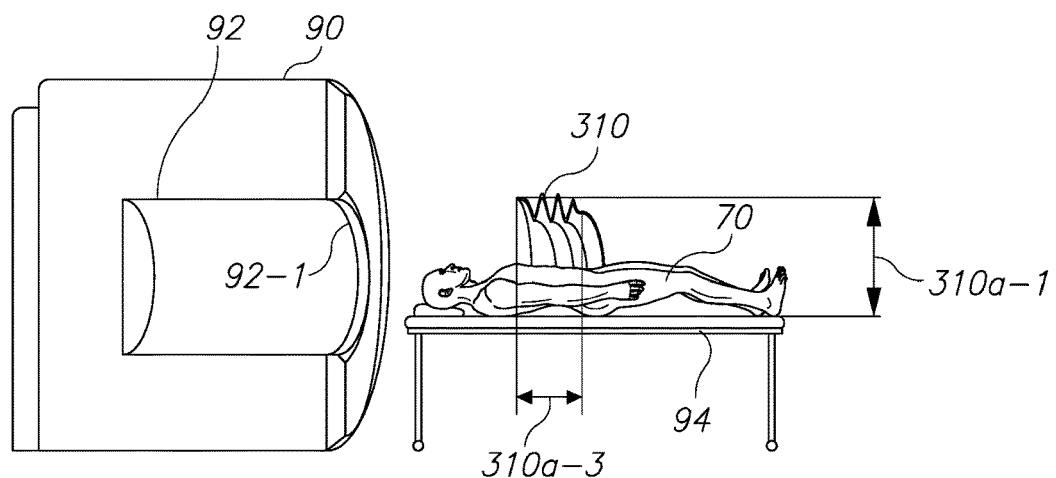
Figure 2B:
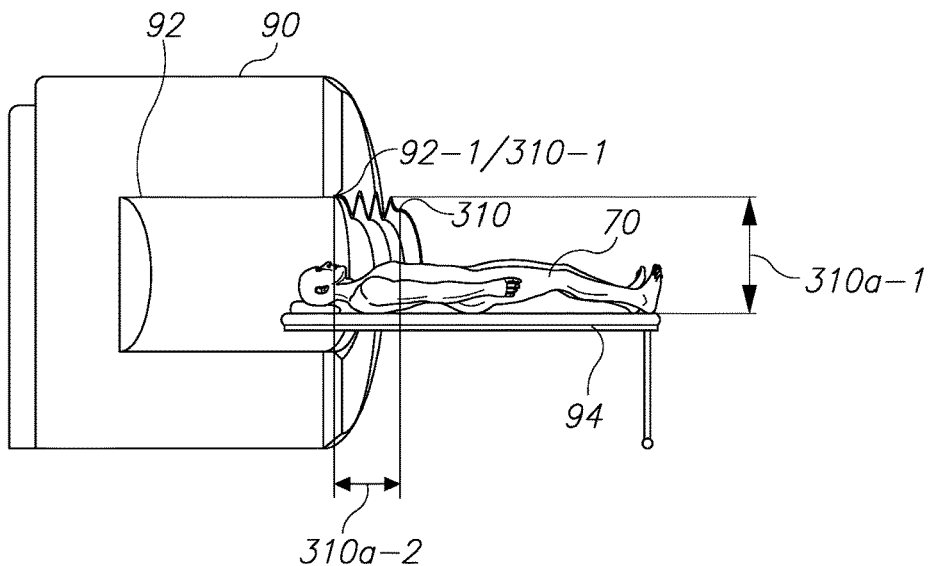

FIGS. 2A-2B are illustration of a RF shielding channel 300 for a magnetic resonance imaging (MRI) device 90, including at least one conductive layer 310 having a U-shape transverse cross-section, according to some embodiments of the invention. FIG. 3A and FIG. 3B provide an isometric view and a longitudinal cross-sectional view of the RF shielding channel 300, respectively. Illustrations 300a, 300b in FIG. 2B show a first initial state and a second initial state of the RF shielding channel 300, where the RF shielding channel 300 is attached to a bed 94 and a bore 92 of the MRI device 90, respectively. Illustration 300c in FIG. 2B shows an extended state of the RF shielding channel 300.

The RF shielding channel 300 can include at least one conductive layer 310 having a substantially U-shape transverse cross-section. The at least on conductive layer 310 can have a proximal end 310-1, a distal end 310-2 and longitudinal edges 310-3. The proximal end 310-1 and a distal end 310-2 can have a transverse dimension (e.g., radius) 310a-1.

The RF shielding channel 300 can include a first connector (not shown) to removably attach the longitudinal edges 310-3 of the at least one conductive layer 310 to the bed 94 of a magnetic resonance imaging (MRI) device 90 such that an electrical path can be established between the at least one conductive layer 310 and the bed 94 (e.g., as in state 300*a* as shown in FIG. 2B). The RF shielding channel 300 can include a second connector (not shown) to removably attach the proximal end of the at least one conductive layer 310 to the bore 92 of the MRI device 90 such that an electrical path can be established between the at least one conductive layer 310 and the bore 92 (e.g., as in state 300*b* as shown in FIG. 2B).

The at least one conductive layer 310 can be extended in a longitudinal direction with respect to the bore 92 between a first predetermined longitudinal dimension 310*a*-3 and a second predetermined longitudinal dimension 310*b*-3 (e.g., as in state 300*c* as shown in FIG. 2B). The at least one conductive layer 310 in the extended state 300*b* can, for example, envelop at least a portion of a patient 70 that is not being imaged. A ratio of the second predetermined longitudinal dimension 310*b*-3 to the transverse dimension 310*a*-1 of the proximal end 310-1 can be at least 5:1 to provide the RF shielding of the MRI device 90 (e.g., by the at least one conductive layer 310 in the extended state 300*c*), as described above with respect to FIGS. 1A-1C and FIG. 1D.

FIGS. 3A-3B are illustrations of a radiofrequency (RF) shielding channel 400 for a magnetic resonance imaging (MRI) device 90, including multiple layers, according to some embodiments of the invention. Illustration 400*a* and illustration 400*b* in FIG. 3A show an isometric view of an initial state and an extended state of the RF shielding channel 400, respectively. Illustration 400*a* in FIG. 3B shows cross-sectional views of the initial state of the RF shielding channel 400.

The RF shielding channel 400 can include at least one conductive layer 410. In some embodiments, the at least one conductive layer 410 is identical to the at least one conductive layer 110, at least one conductive layer 210 and/or at least one conductive layer 310 as shown in FIGS. 1A-1C, FIG. 1D and FIGS. 2A-2B, respectively. The at least one conductive layer 410 can have a proximal end 410-1 and a distal end 410-2.

The RF shielding channel 400 can include a connector (not shown) to removably attach the proximal end 410-1 of the at least one conductive layer 410 to a bore 92 of the MRI device 90 (e.g., as described above with respect to FIGS. 1A-1C, FIG. 1D and FIGS. 2A-2B). The at least one conductive layer 410 can be extended in a longitudinal dimension along the conductive layer between a first predetermined longitudinal dimension 410*a*-3 and a second predetermined longitudinal dimension 410*b*-3. A ratio of the second predetermined longitudinal dimension 410*b*-3 to the transverse dimension 410*a*-1 of the proximal end 410-1 can be at least 5:1 to provide the RF shielding of the MRI device 90 (e.g., by the at least one conductive layer 410 in extended state 400*b*), as described above with respect to FIGS. 1A-C, FIG. 1D and FIGS. 2A-2B.

In some embodiments, the RF shielding channel 400 includes an inner layer 411 and/or an outer layer 412. The inner and/or outer layers 411, 412, respectively, can surround the at least one conductive layer 410 and/or can be connected to the distal end 410-2 of the at least one conductive layer 410. The inner and/or outer layers 411, 412 can be made of foldable material (e.g., a fabric material). In some embodiments, a length of the inner and/or outer layers 411, 412 in the initial state 400*a* is greater than the first predetermined longitudinal dimension 410*a*-3 of the at least one conductive layer 410. Accordingly, the inner and/or outer layers 411, 412 can be packed around the at least one conductive layer 410 to include a plurality of folds 413 (e.g., as shown on the left-hand side in FIG. 3A).

The inner and/or outer layers 411, 412, respectively, can unfold, upon extension of the at least one conductive layer 410 from the first predetermined longitudinal dimension 410*a*-3 to the second predetermined longitudinal dimension 410*b*-3 (e.g., as shown on the right-hand side in FIG. 3A). The inner and/or outer layers 411, 412, respectively, can fold, upon contraction of the at least one conductive layer 410 from the second predetermined longitudinal dimension 410*b*-3 to the first predetermined longitudinal dimension 410*a*-3 (e.g., as shown on the left-hand side in FIG. 3A).

In some embodiments, the RF shielding channel 400 includes an extendable layer 415. The extendable layer 415 can be positioned between the inner and outer layers 411, 412, respectively (e.g., as shown in FIG. 3B). The extendable layer 415 can be connected to the distal end 410-2 of the at least one conductive layer 410. The extendable layer 415 can be made of, for example, an elastic material (e.g., latex).

In various embodiments, the at least one conductive layer 410 is associated with at least one of the inner layer 411, outer layer 412, extendable layer 415 and/or any combination thereof. In various embodiments, the at least one conductive layer 410 is embedded within the least one of the inner layer 411, outer layer 412, extendable layer 415 and/or any combination thereof.

The RF shielding channel 400 can include a gap 417 between the inner and extendable layers 411, 415, respectively (e.g., as shown in FIG. 3B). The gap 417 can include a fluid, for example, air.

In some embodiments, the at least one conductive layer 410 extends from the first predetermined longitudinal dimension 410*a*-3 to the second predetermined longitudinal dimension 410*b*-3 upon an increase of a fluid pressure in the gap 417. Upon the increase of the fluid pressure in the gap 417, the extendable layer 415 (e.g., that can be made of the elastic material) can extend in a transverse and/or a longitudinal directions. The inner and/or outer layers 411, 412, respectively (e.g., that can be made of the fabric material and thus can be inextensible) can unfold and extend substantially in the longitudinal direction, thereby restricting the extension of the extendable layer 415 in the transverse direction. As a result, the extendable layer 415 and/or the at least one conductive layer 410 can extend substantially in the longitudinal direction along the channel to the second predetermined longitudinal dimension 410*b*-3.

In some embodiments, the at least one conductive layer 410 contracts from the second predetermined longitudinal dimension 410*b*-3 to the first predetermined longitudinal dimension 410*a*-3 upon a decrease of the fluid pressure in the gap 417. Upon the decrease of the fluid pressure in the gap 417, the extendable layer 415 can contract to its initial transverse and/or longitudinal dimensions (e.g., due to elasticity of the extendable layer 415). The inner and/or outer layers 411, 412, respectively (that can be connected to the at least one conductive layer 410 and/or to the extendable layer 415 at the distal end 410-2) can be folded and/or packed around the at least one conductive layer 410.

In various embodiments, the RF shielding channel 100 (e.g., as described above with respect to FIGS. 1A-1C), RF shielding channel 200 (e.g., as described above with respect to FIG. 1D) and/or RF shielding channel 300 (e.g., as described above with respect to FIGS. 2A-2B) are identical to the RF shielding channel 400 and/or include at least one of: the inner layer 411, outer layer 412 and/or extendable layer 415.

In some embodiments, the RF shielding channel (e.g., the RF channel 400 as described with respect to FIGS. 3A-3B) has a telescopic structure (not shown). The telescopic RF shielding channel can include a plurality of stages. Each of the plurality of the stages can include at least one conductive layer (e.g., conductive layer 410 as described above with respect to FIGS. 3A-3B). Each of the plurality of stages can also include at least a portion of the inner layer 411, outer layer 412 and/or extendable layer 415 (e.g., as described above with respect to FIGS. 3A-3B). In various embodiments, the telescopic RF shielding channel is extended and/or contracted in a longitudinal direction with respect to the bore 92 of the MRI device 90 manually and/or using a dedicated mechanism (not shown).

Figure 4A:
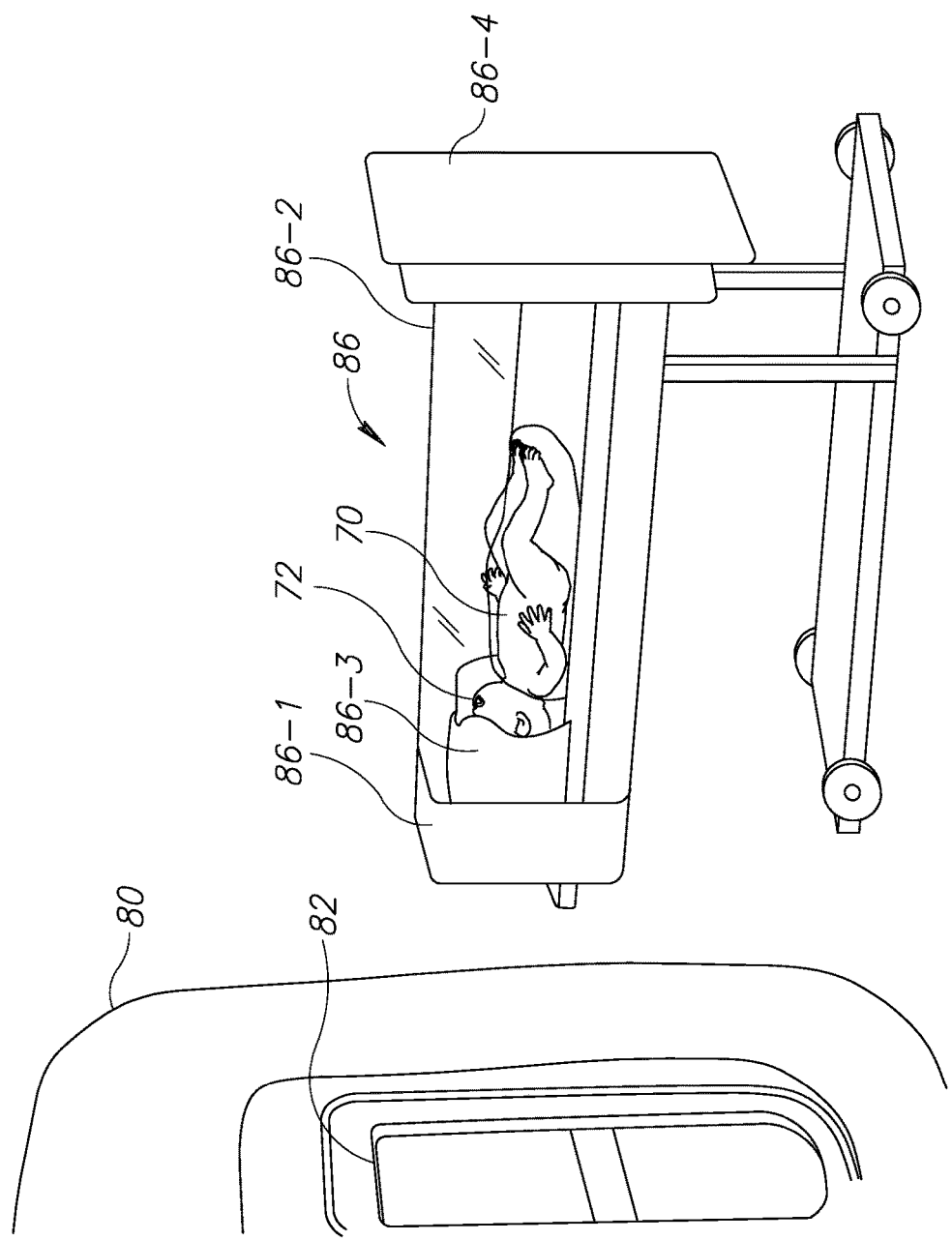

FIGS. 4A-4C are illustrations of a radiofrequency (RF) shielding channel 500 for an incubator 86 for positioning a patient 70 in a magnetic resonance imaging (MRI) device 80, according to some embodiments of the invention.

FIG. 4A presents an isometric view of the incubator 86 and the MRI device 80. The incubator 86 can have a proximal end 86-1 and a distal end 86-2. The incubator 86 can accommodate the patient (e.g., a neonate) 70 and/or can be inserted to a bore 82 of the MRI device 80 via the distal end 86-2 such that the proximal end 86-1 mates with an aperture of the bore 82. In some embodiments, the incubator 86 includes a RF coil unit 86-3 positioned at the distal end 86-2. The RF coil unit 86-3 can generate a magnetic field and/or RF signals to perform an imaging of at least a portion of the patient (e.g., a head 72 of the neonate 70, as shown in FIGS. 4A-4C). In some embodiments, the incubator 86 has a closure 86-4 coupled to the proximal end 86-1. The closure 86-4 can prevent, upon a shutting of the closure 86-4 onto the bore 82, an external RF radiation from entering the bore 82 and/or an RF radiation emitted by the MRI device 80 and/or the RF coil unit 86-3 from exiting the bore 82.

FIGS. 4B-4C present a top view of the RF shielding shieling 500 for the incubator 86. Illustration 500a and illustration 500b in FIGS. 4B-4C indicate an initial state and an extended state of the RF shielding channel 500, respectively.

The RF shielding channel 500 can include at least one conductive layer 510. The at least one conductive layer 510 can be similar to the at least one conductive layer 110 (e.g., as described above with respect to FIGS. 1A-1C), at least one conductive layer 210 (e.g., as described above with respect to FIG. 1D), at least one conductive layer 310 (e.g., as described above with respect to FIGS. 2A-2B) and/or at least one conductive layer 410 (e.g., as described above with respect to FIGS. 3A-3B). The at least one conductive layer 510 can have a proximal end 510-1 and a distal end 510-2. The proximal and/or the distal ends 510-1, 510-2, respectively can have a transverse dimension (e.g., length and/or width) 510a-1 (e.g., as shown in FIGS. 4B-4C).

The RF shielding channel 500 can include a connector (not shown) to removably attach the proximal end 510-1 of the at least one conductive layer 510 to the proximal end 86-1 of the incubator 86 such that an electrical path can be established between the at least one conductive layer 510 and the incubator 86. In some embodiments, a transverse cross-section of the at least one conductive layer 510 corresponds to a transverse cross-section of the incubator 86 (e.g., a substantially rectangular cross-section, as shown in FIGS. 4A-4C). In various embodiments, the proximal end 510-1 of the at least one conductive layer 510 is removably attached to inner surfaces 86-8 (e.g., as shown in FIG. 4B) and/or to outer surfaces 86-9 (e.g., as shown in FIG. 4C) of the incubator 86.

The at least one conductive layer 510 can be extended in a longitudinal direction with respect to the incubator 86 between a first predetermined longitudinal dimension 510a-3 and a second predetermined longitudinal dimension 510b-3 (e.g., as in state 500b as shown in FIGS. 4B-4C) to, for example, envelope at least a portion of the neonate 70 that is not being imaged. A ratio of the second predetermined longitudinal dimension 510b-3 and the transverse dimension 510a-1 of the proximal end 510-1 can be at least 5:1 such that a RF shield is formed from the proximal end 86-1 of the incubator 86 to the distal end 510-2 of the at least one conductive layer 510.

The RF shield can prevent (e.g., by the at least one conductive layer 510 in the extended state 500b) an external RF radiation from entering the bore 82 of the MRI device 80 and/or an RF radiation emitted by the MRI device 80 and/or the RF coil unit 86-3 from exiting the bore 82. Accordingly, the RF shielding channel 500 can enable operating the MRI device 80 in a RF environment while eliminating a need in the closure 86-4 of the incubator 86. One advantage of eliminating a need in the closure 86-4 can include enabling easily and/or quickly pulling out the neonate 70 from the incubator 86 in a case of emergency.

In various embodiments, the RF shielding channel 500 is identical to the RF shielding channel 400 and/or includes at least one of: the inner layer 411, outer layer 412 and/or extendable layer 415 (e.g., as described above with respect to FIGS. 3A-3B).

Figure 5A:
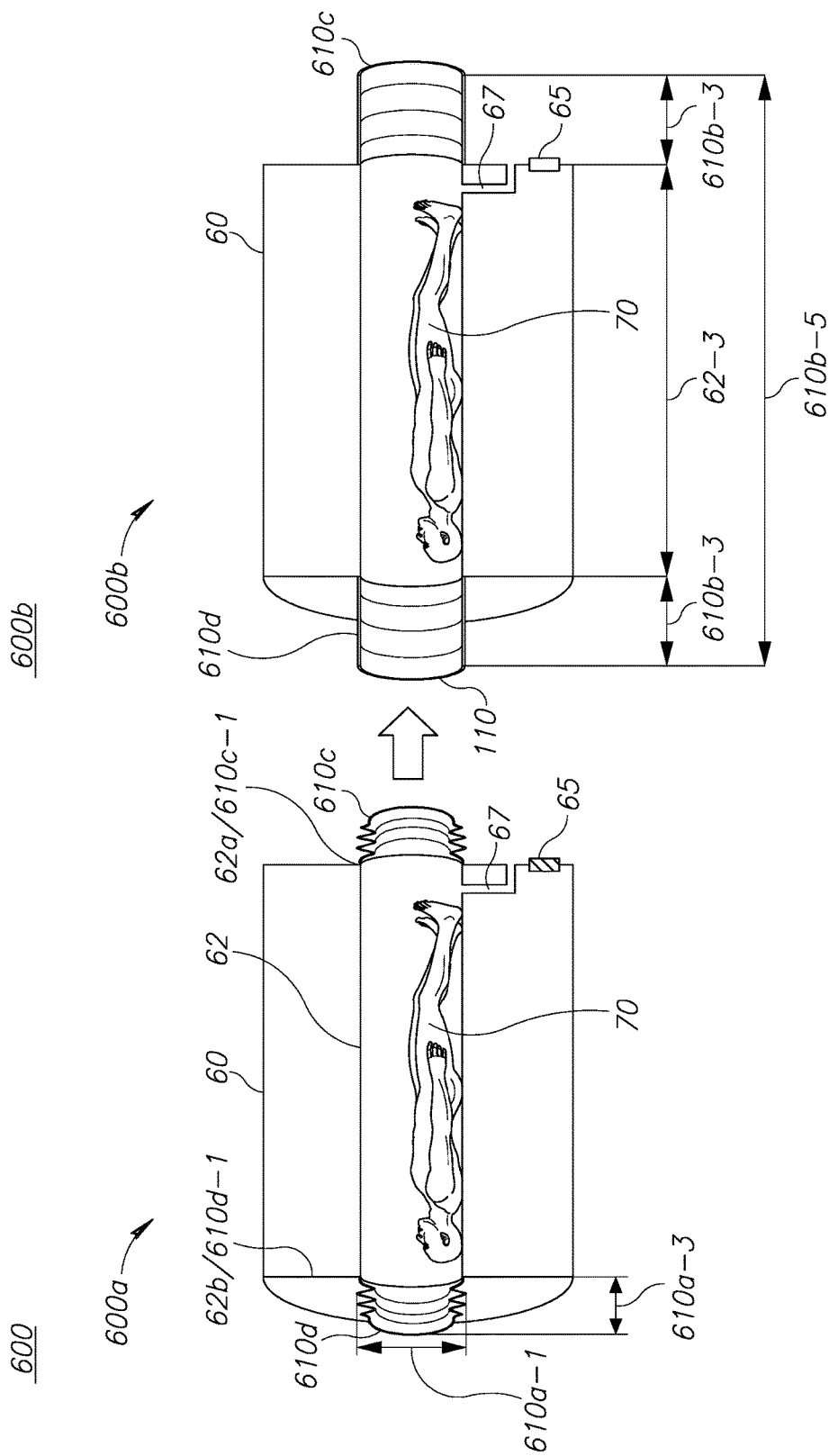
FIG. 5A is an illustration of a set of radiofrequency (RF) shielding channels for a full body open bore magnetic resonance imaging (MRI) device, according to some embodiments of the invention.

FIG. 5A is an illustration of a set 600 of radiofrequency (RF) shielding channels 600c, 600d for a full body open bore magnetic resonance imaging (MRI) device 60, according to some embodiments of the invention. Illustration 600a and illustration 600b in FIG. 5A indicate an initial state and an extended state of the RF shielding channels 600c, 600d, respectively.

The set 600 can include a first and/or second RF shielding channel 600c, 600d, respectively. Each of the first and/or second RF shielding channels 600c, 600d can be identical to the RF shielding channels 100, 200 and/or 400 as described above with respect to FIGS. 1A-1C, FIG. 1D and FIGS. 3A-3B, respectively.

Each of the first and/or second RF shielding channels 600c, 600d can include at least one conductive layer 610c, 610d, respectively. Each of the at least one conductive layers 610c, 610d can have proximal ends 610c-1, 610d-1, respectively and distal ends 610c-2, 610d-2. The proximal and distal ends 610c-1, 610d-1 and 610c-2, 610d-2 respectively, can have a transverse dimension (e.g., diameter) 610a-1.

The MRI device 60 can include a bore 62 having two apertures 62a, 62b positioned at opposite sides along a longitudinal axis of the MRI device 60 (e.g., as shown in FIG. 5A). In some embodiments, the MRI device 60 utilizes at least one superconductive magnet to generate a magnetic field. In some embodiments, the MRI device 60 includes a RF panel 65 and/or RF tunnel 67. The RF tunnel 67 can enclose a RF wiring and/or medical tubing (e.g., connected to a patient 70) extending from an external environment into the bore 62 and/or into the MRI device 60.

The proximal end 610c-1 of the at least one conductive layer 610c can be removably attached to the aperture 62a of the bore 62 and/or the proximal end 610d-1 of the at least one conductive layer 610d can be removably attached to the aperture 62b of the bore 62. Each of the at least one conductive layers 610c, 610d can be extended in a longitudinal direction with respect to the bore 62 between a first predetermined longitudinal dimension 610*a*-3 and a second predetermined longitudinal dimension 610*b*-3 to form a RF shielding tunnel (e.g., as shown on the right-hand side in FIG. 5A). The RF shielding tunnel can include the at least one conductive layers 610*c*, 610*d* in the extended state 600*b* and/or the bore 62 of the MRI device 60. The RF shielding tunnel can have a longitudinal dimension 610*b*-5 that can include a length 62-3 of the bore 62 and/or the length (e.g., the second predetermined longitudinal dimension 610*b*-3) of the at least one conductive layers 610*c*, 610*d* (e.g., as shown in FIG. 5A). A ratio of the longitudinal dimension 610*b*-5 to transverse dimension 610*a*-1 of the proximal end 610-1 of the at least one conductive layers 610*c*, 610*d* can be at least 5:1 such that the RF shielding tunnel can provide the RF shielding of the MRI device 60 (e.g., as described above with respect to FIGS. 1A-1C).

Figure 5B:
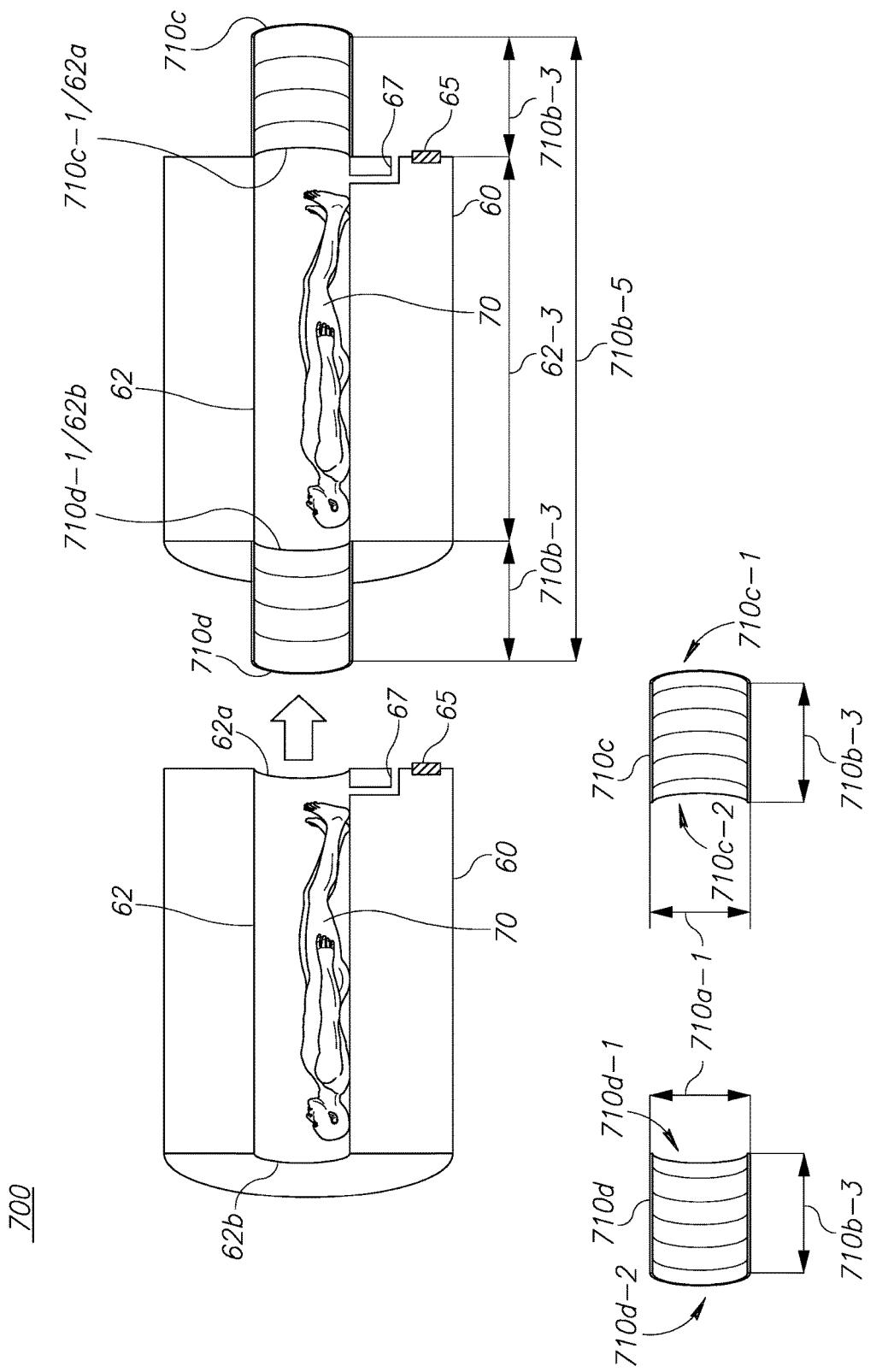
FIG. 5B is an illustration of a set of non-extendable radiofrequency (RF) shielding channels for a full body open bore magnetic resonance imaging (MRI) device, according to some embodiments of the invention.

FIG. 5B is an illustration of a set 700 of non-extendable radiofrequency (RF) shielding channels 700*c*, 700*d* for a full body open bore magnetic resonance imaging (MRI) device 60, according to some embodiments of the invention.

The set 700 can include a first and/or second RF shielding channel 700*c*, 700*d*, respectively. Each of the first and/or second RF shielding channels 700*c*, 700*d* can include at least one conductive layer 710*c*, 710*d*, respectively. The at least one conductive layers 710*c*, 710*d* can have proximal ends 710*c*-1, 710*d*-1 and distal ends 710*c*-2, 710*d*-2. The proximal and distal ends 710*c*-1, 710*d*-1 and 710*c*-2, 710*d*-2 respectively, can have a transverse dimension (e.g., diameter) 710*a*-1. The at least one conductive layers 710*c*, 710*d* can be not extendable and/or can have a constant predetermined longitudinal dimension 710*b*-3. In various embodiments, each of the first and/or second RF shielding channels 700*c*, 700*d*, respectively include at least one of: an inner and/or outer layer (e.g., that can be similar to the inner and outer layers 411, 412, as described above with respect to FIGS. 3A-3B).

The proximal end 710*c*-1 of the at least one conductive layer 710*c* can be removably attached to the aperture 62*a* of the bore 62 and/or the proximal end 710*d*-1 of the at least one conductive layer 710*d* can be removably attached to the aperture 62*b* of the bore 62 to form a RF shielding tunnel. The RF shielding tunnel can include the at least one conductive layers 710*c*, 710*d* and/or the bore 62 of the MRI device 60. The RF shielding tunnel can have a longitudinal dimension 710*b*-5 that can include the length 62-3 of the bore 62 and/or the length (e. g., the second predetermined longitudinal dimension 710*b*-3) of the at least one conductive layers 710*c*, 710*d* (e.g., as shown in FIG. 5B). A ratio of the longitudinal dimension 710*b*-5 to transverse dimension 710*a*-1 of the proximal end 710*c*-1, 710*d*-1 of the at least one conductive layers 710*c*, 710*d* can be at least 5:1 such that the RF shielding tunnel can provide the RF shielding of the MRI device 60 (e.g., as described above with respect to FIGS. 1A-1C).

Figure 5C:
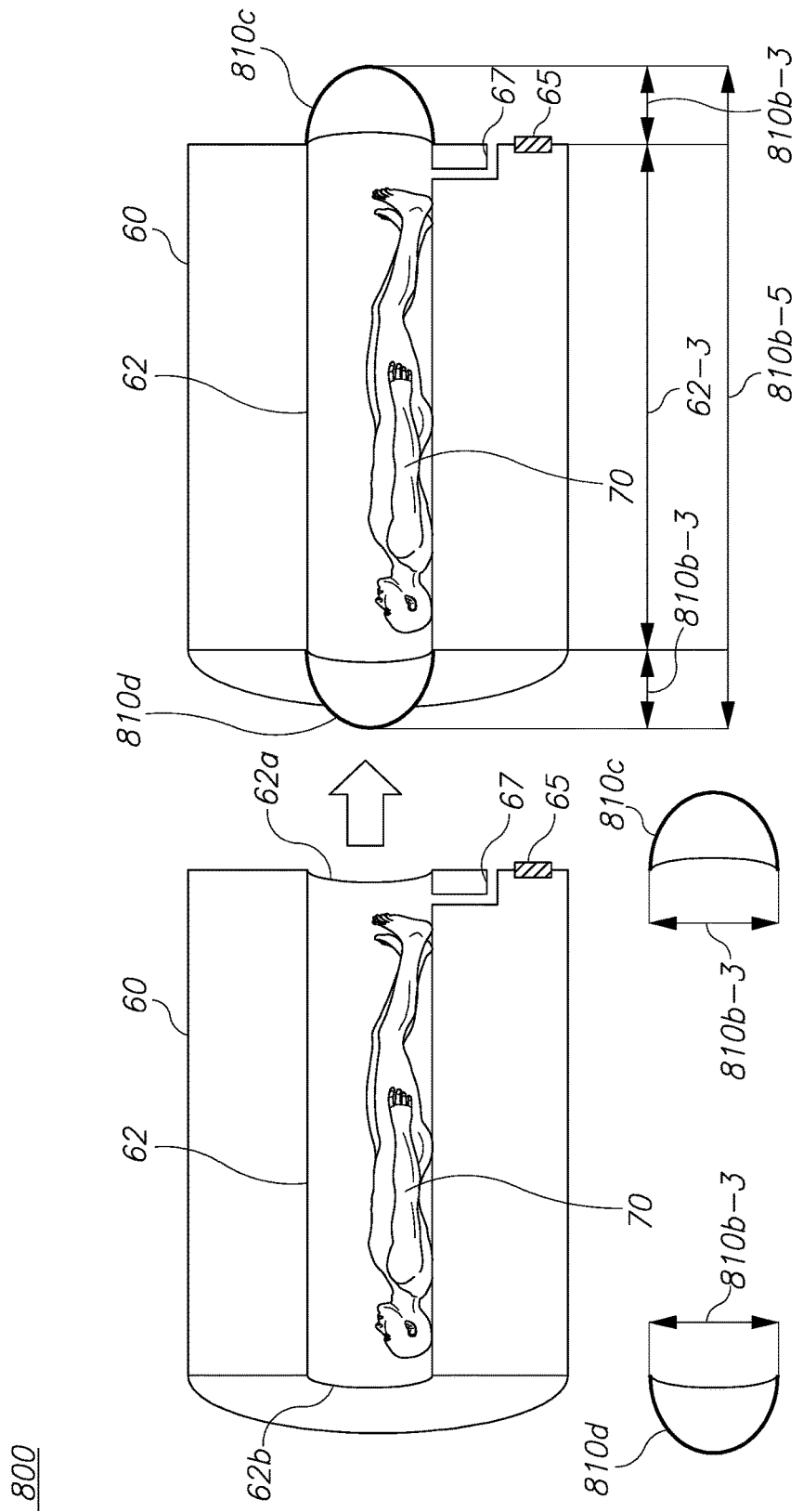
FIG. 5C is an illustration of a set of radiofrequency (RF) shields for a full body open bore magnetic resonance imaging (MRI) device, having a hemispherical shape, according to some embodiments of the invention.

FIG. 5C is an illustration of a set 800 of radiofrequency (RF) shields 800*c*, 800*d* for a full body open bore magnetic resonance imaging (MRI) device 60, having a hemispherical shape, according to some embodiments of the invention.

The set 800 can include a first and/or second RF shield 800*c*, 800*d* having a hemispherical shape. Each of the first and/or second RF shielding shields 800*c*, 800*d* can include at least one conductive layer 810*c*, 810*d*. The at least one conductive layers 810*c*, 810*d* can be not extendable and/or can have a constant predetermined transverse dimension 810*b*-3.

The at least one conductive layer 810*c* of first RF shield 800*c* can be removably attached to the aperture 62*a* and/or the at least one conductive layer 810*d* of the second RF shield 800*d* can be removably attached to the aperture 62*b* to form a RF shielding tunnel. The RF shielding tunnel can include the at least one conductive layer 810*c*, 810*d* and/or the bore 62 of the MRI device 60. The RF shielding tunnel can have a longitudinal dimension 810*b*-5 that can include the length 72-3 of the bore 62 and/or the transverse dimension 810*b*-3 of the at least one conductive layers 810*c*, 810*d* (e.g., as shown in FIG. 5C). A ratio of the length 810*b*-5 to transverse dimension 810*b*-3 of the at least one conductive layers 810*c*, 810 *d* can be at least 5:1 such that the RF shielding tunnel can provide the RF shielding of the MRI device 60 (e.g., as described above with respect to FIGS. 1A-1C).

Figure 5D:
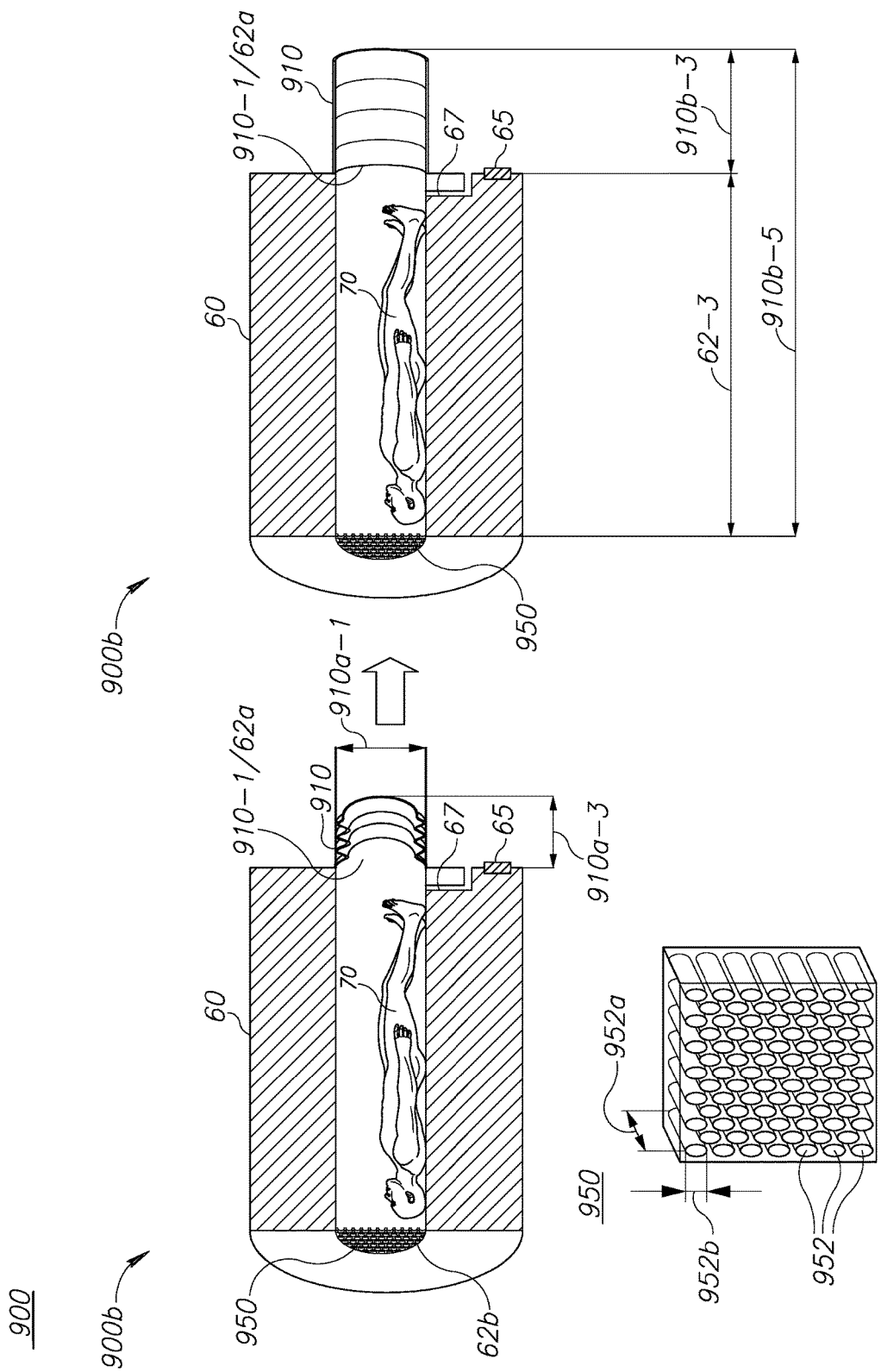
FIG. 5D is an illustration of a set including a radiofrequency (RF) channel and a RF shield cover for a full body open bore magnetic resonance imaging (MRI) device, according to some embodiments of the invention.

FIG. 5D is an illustration of a set 900 including a radiofrequency (RF) channel 900*c* and a RF shield cover 950 for a full body open bore magnetic resonance imaging (MRI) device 60, according to some embodiments of the invention. Illustration 900*a* and illustration 900*b* in FIG. 5D indicate an initial state and an extended state of the RF shielding channel 900*c*, respectively.

The set 900 can include a RF shielding channel 900*c*. In various embodiments, the RF shielding channel 900*c* is identical to the RF shielding channels 100, 200, 400 600*c* and/or 600*d* as described above with respect to FIGS. 1A-1C, FIG. 1D, FIGS. 3A-3B and FIG. 5A, respectively.

The RF shielding channel 900*c* can include at least one conductive layer 910. The at least one conductive layer 910 can have a proximal end 910-1 and a distal end 910-2. The proximal end 910-1 and/or the distal end 910-2 can have a transverse dimension 910*a*-1.

The proximal end 910-1 of the at least one conductive layer 910 can be removably attached to the aperture 62*a* of the bore 62 of the MRI device 60. The at least one conductive layer 910 can be extended in a longitudinal direction with respect to the bore 62 between a first predetermined longitudinal dimension 910*a*-3 and a second predetermined longitudinal dimension 910*b*-3 to form a RF shielding tunnel (e.g., as shown on the right-hand side in FIG. 5D). The RF shielding tunnel can include the at least one conductive layer 910 in the extended state 900*b* and/or the bore 62 of the MRI device 60. The RF shielding tunnel can have a longitudinal dimension 910*b*-5 that can include a length 62-3 of the bore 62 and/or the length (e.g., the second predetermined longitudinal dimension 910*b*-3) of the at least one conductive layer 910 (e.g., shown in FIG. 5D). A ratio of the longitudinal dimension 910*b*-5 to transverse dimension 910*a*-1 of the proximal end 910-1 of the at least one conductive layer 910 can be at least 5:1 such that the RF shielding tunnel can prevent from an external RF radiation from entering the bore 62 via aperture 62*a* and/or from an RF radiation emitted by the MRI device 60 from exiting the bore 62 via aperture 62*a*.

The set 900 can include a RF shielding cover 950. The RF shielding cover 950 can cover the aperture 62*b* of the bore 62. The RF shielding cover 950 can prevent an external RF radiation from entering the bore 62 via the aperture 62*b* and/or an RF radiation emitted by the MRI device 60 from exiting the bore 62 via the aperture 62*b*.

The RF shielding cover 950 can include a plurality of holes 952 (e.g., as shown in FIG. 5D), where each of the holes 952 can have a length 952*a* and a diameter 952*b*. In some embodiments, a ratio of the length 952*a* to the diameter 952*b* of each hole 952 is at least 5:1. The holes 952 are circle shaped. In various embodiments, the holes 952 are square, rectangular, oval, or any shape. In these various shaped embodiments, each hole can have a ratio of length to width of at least 5:1. In various embodiments, the RF shield 950 is a mesh, a net and/or any combination thereof.

Figure 5E:
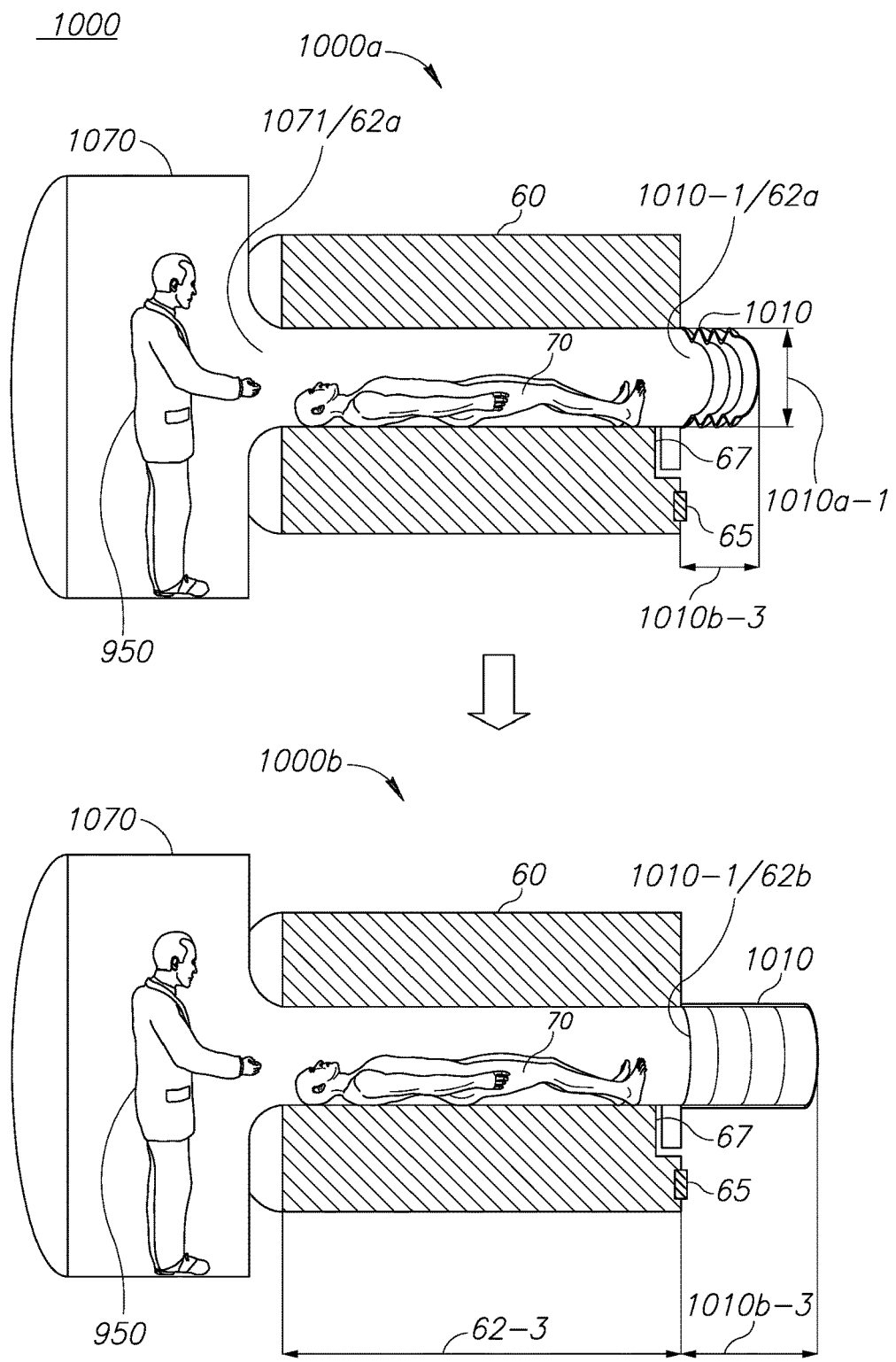
FIG. 5E is an illustration of a set including a radiofrequency (RF) channel and a RF shielding shell for a full body open bore magnetic resonance imaging (MRI) device, according to some embodiments of the invention.

FIG. 5E is an illustration of a set 1000 including a radiofrequency (RF) channel 1000c and a RF shielding shell 970 for a full body open bore magnetic resonance imaging (MRI) device 60, according to some embodiments of the invention. Illustration 1000a and illustration 1000b in FIG. 5E indicate an initial state and an extended state of the RF shielding channel 1000c, respectively.

The set 1000 can include a RF shielding channel 1000c. In various embodiments, the RF shielding channel 1000c is identical to the RF shielding channels 100, 200, 400 600c, 600d and/or 900c as described above with respect to FIGS. 1A-1C, FIG. 1D, FIGS. 3A-3B, FIG. 5A and FIG. 5D, respectively.

The RF shielding channel 1000c can include at least one conductive layer 1010. The at least one conductive layer 1010 can gave a proximal end 1010-1 and a distal end 1010-2. The proximal end 1010-1 and/or the distal end 1010-2 can have a transverse dimension 1010a-1.

The proximal end 1010-1 of the at least one conductive layer 1010 can be removably attached to the aperture 62a of the bore 62 of the MRI device 60. The at least one conductive layer 1010 can be extended in a longitudinal direction with respect to the bore 62 between a first predetermined longitudinal dimension 1010a-3 and a second predetermined longitudinal dimension 1010b-3 to form a RF shielding tunnel (e.g., as shown on the right-hand side in FIG. 5E). The RF shielding tunnel can include the at least one conductive layer 1010 in the extended state 1010b and/or the bore 62 of the MRI device 60. The RF shielding tunnel can have a longitudinal dimension 1010b-5 that can include a length 62-3 of the bore 62 and/or the length (e.g., the second predetermined longitudinal dimension 1010b-3) of the at least one conductive layer 1010 (e.g., shown in FIG. 5D). A ratio of the longitudinal dimension 1010b-5 to transverse dimension 1010a-1 of the proximal end 1010-1 of the at least one conductive layer 1010 can be at least 5:1 such that the RF shielding tunnel can prevent from an external RF radiation from entering the bore 62 via aperture 62a and/or from an RF radiation emitted by the MRI device 60 from exiting the bore 62 via aperture 62a.

The set 1000 can include a RF shielding shell 1070. The RF shielding shell 1070 can be adapted to accommodate at least a person 50, for example a physician. The RF shielding shell 1070 can include a first opening 1071. The first opening 1071 can be removably attached to the aperture 62b of the bore 62 such that an electrical path can be established between the bore 62 and the RF shielding shell 1070. The RF shielding shell 1070 can be made for a conductive and/or nonmagnetic metal (e.g., copper, aluminum, and/or other suitable material as is known in the art). The RF shielding shell 1070 can prevent, upon connection to the aperture 62a, an external RF radiation from entering the bore 62 via aperture 62b and/or from an RF radiation emitted by the MRI device 60 from exiting the bore 62 via aperture 62b.

The RF shielding shell 1070 can be adapted to provide the person 50 an access to the patient 70 (e.g., through the first opening 1071 and the aperture 62b) within the MRI device 60. For example, person 50 can be a physician that can operate the patient 70 while undergoing an MRI scan using medical tools made, for example, from a non-magnetic material. The RF shielding shell 1070 can include at least one second opening (not shown) to enable the person 50 to enter into interior of the RF shielding shell 1070 while it is connected to the aperture 62b of the bore 62.

Generally, the present invention discloses RF shieling channels (e.g., the RF shielding channel 100 as described above with respect to FIG. 1A) that can be removably attached to a bore of a MRI device (e.g., the MRI device 90 and/or the MRI device 60 as described above with respect to FIG. 1A and FIG. 5A, respectively). The RF shielding channels can be extended to a predetermined longitudinal dimension with respect to the bore to provide a RF shielding of the MRI device. The RF shielding of the MRI device can include preventing an external RF radiation from entering the bore of the MRI device and/or an RF radiation emitted by the MRI device from exiting the bore. Accordingly, one advantage of the present invention can include enabling an operation of the MRI device in a RF environment while eliminating a need in a dedicated MRI room.

In the above description, an embodiment is an example or implementation of the invention. The various appearances of "one embodiment", "an embodiment", "certain embodiments" or "some embodiments" do not necessarily all refer to the same embodiments. Although various features of the invention may be described in the context of a single embodiment, the features may also be provided separately or in any suitable combination. Conversely, although the invention may be described herein in the context of separate embodiments for clarity, the invention may also be implemented in a single embodiment. Certain embodiments of the invention may include features from different embodiments disclosed above, and certain embodiments may incorporate elements from other embodiments disclosed above. The disclosure of elements of the invention in the context of a specific embodiment is not to be taken as limiting their use in the specific embodiment alone. Furthermore, it is to be understood that the invention can be carried out or practiced in various ways and that the invention can be implemented in certain embodiments other than the ones outlined in the description above.

The invention is not limited to those diagrams or to the corresponding descriptions. For example, flow need not move through each illustrated box or state, or in exactly the same order as illustrated and described. Meanings of technical and scientific terms used herein are to be commonly understood as by one of ordinary skill in the art to which the invention belongs, unless otherwise defined. While the invention has been described with respect to a limited number of embodiments, these should not be construed as limitations on the scope of the invention, but rather as exemplifications of some of the preferred embodiments. Other possible variations, modifications, and applications are also within the scope of the invention. Accordingly, the scope of the invention should not be limited by what has thus far been described, but by the appended claims and their legal equivalents.

The invention claimed is:

1. A radiofrequency (RF) shielding channel for a magnetic resonance imaging (MRI) device, the RF shielding channel comprising:
   at least one conductive layer having a proximal end and a distal end, the at least one conductive layer extendable in a longitudinal direction with respect to a bore of the MRI device between a first predetermined longitudinal dimension and a second predetermined longitudinal dimension; and
   a connector to connect the proximal end of the at least one conductive layer to the bore of the MRI device, such that a RF shield is formed from the bore of the MRI device to the distal end of the at least one conductive layer upon extension of the at least one conductive layer to the second predetermined longitudinal dimension such that RF radiation emitting from the bore is substantially prevented from exiting the distal end of the at least one conductive layer, and RF radiation emitting from an environment external to the MRI device is substantially prevented from entering the bore.

2. The RF shielding channel of claim 1, further comprising:
an inner layer and an outer layer surrounding the at least one conductive layer and connected to the distal end of the at least one conductive layer, the inner layer and the outer layer are made of foldable material and comprising a plurality of folds,
wherein the inner layer and the outer layer unfold, upon extension of the at least one conductive layer to the second predetermined longitudinal dimension, and fold, upon contraction of the at least one conductive layer to the first predetermined longitudinal dimension.

3. The RF shielding channel of claim 2, further comprising:
an extendable layer positioned between the inner layer and the outer layer and connected to the distal end of the at least one conductive layer,
wherein the extendable layer to extend the at least one conductive layer to the second predetermined longitudinal dimension and to unfold the inner and the outer layer, and wherein the extendable layer to contract the at least one conductive layer to the first predetermined longitudinal dimension and to fold the inner layer and the outer layer.

4. The RF shielding channel of claim 3, further comprising a gap between the inner layer and the extendable layer, wherein the gap comprises a fluid.

5. The RF shielding channel of claim 4, wherein the extendable layer extends upon an increase of a fluid pressure within the gap and wherein the extendable layer contracts upon decrease of the fluid pressure within the gap.

6. The RF shielding channel of claim 1, wherein the at least one conductive layer having a transverse dimension and wherein a ratio of the second predetermined longitudinal dimension to the transverse dimension is at least 5:1.

7. The RF shielding channel of claim 1, wherein the at least one conductive layer having a tapered shape in the longitudinal direction with respect to the bore of the MRI device.

8. The RF shielding channel of claim 1, wherein the at least one conductive layer having a substantially U-shape transversal cross-section and wherein the at least one conductive layer is connected to a bed of the MRI device such that the bed being a part of the RF shielding channel.

9. The RF shielding channel of claim 1, wherein the proximal end of the at least one conductive layer is connected to an aperture of the bore of the MRI device.

10. The RF shielding channel of claim 1, wherein the at least conductive layer at least partly envelops at least a portion of a patient that is not being imaged by the MRI device.

11. The RF shielding channel of claim 1, wherein an electrical path is established between the at least one conductive layer and the bore of the MRI device.

12. The RF shielding channel of claim 1, wherein the MRI device utilizes at least one of: permanent magnets, superconductive magnets or any combination thereof to generate a magnetic field.

* * * * *